United States Patent [19]

Naik et al.

[11] Patent Number: 5,292,751

[45] Date of Patent: Mar. 8, 1994

[54] 5,7-DIHYDROXY-2-METHYL-8-(4-(3-HYDROXY-1-(1-PROPYL))PIPERIDINYL)-4H-1-BENZOPYRAN-4-ONE, ITS PREPARATION AND ITS USE

[75] Inventors: Ramachandra G. Naik, Mulund; Shrikant V. Rao, Dombivili (West); Aftab D. Lakdawala, Bombay; Mandakini V. Shirole, Thane; Bansi Lal, Mulund (West); Noel J. de Souza, Bandra, all of India; Jürgen Blumbach, Niedernhausen, Fed. Rep. of Germany

[73] Assignee: Hoechst Aktiengesellschaft, Frankfurt am Main, Fed. Rep. of Germany

[21] Appl. No.: 865,247

[22] Filed: Apr. 8, 1992

[30] Foreign Application Priority Data

Apr. 10, 1991 [EP] European Pat. Off. ........ 91105643.0

[51] Int. Cl.$^5$ .................. A61K 31/445; C07D 405/04
[52] U.S. Cl. ..................................... 514/320; 546/196
[58] Field of Search .......................... 546/196; 514/320

[56] References Cited

U.S. PATENT DOCUMENTS 4,900,727 2/1990 Kattige ................................. 546/193

FOREIGN PATENT DOCUMENTS 0137193 4/1985 European Pat. Off. .
0241003 10/1987 European Pat. Off. .
0366061 2/1990 European Pat. Off. .... C07D 405/04

OTHER PUBLICATIONS

The Structure Of Rohitukene, The Main Alkaloid Of Amoora Rohituka (Syn. Aphanamixis Polystachya) (Meliaceae), A. D. Harmon et al., Tetrahedron Letters, No. 8, (1979) pp. 721–724.

An Antiinflammatory Cum Immunomodulatory Piperidinylbenzopyranone From Dysoxylum Binectariferum : Isolation, Structure and Total Synthesis, R. A. Naik et al., Tetrahedron vol. 44, No. 7, (1988) pp. 2081–2086.

Primary Examiner—Bernard Dentz
Assistant Examiner—Celia Chang
Attorney, Agent, or Firm—Finnegan, Henderson Farabow, Garrett & Dunner

[57] ABSTRACT

The present invention relates to 5,7-Dihydroxy-2-methyl-8-[4-(3-hydroxy-1-(1-propyl))piperidinyl]-4H-1-benzopyran-4-one its preparation and its use.

5,7-Dihydroxy-2-methyl-8-[4-(3-hydroxy-1-(1-propyl))piperidinyl]-4H-1-benzopyran-4-one is useful for the treatment of arthritis and/or rheumatism and for the treatment of chronic inflammatory diseases.

6 Claims, 3 Drawing Sheets

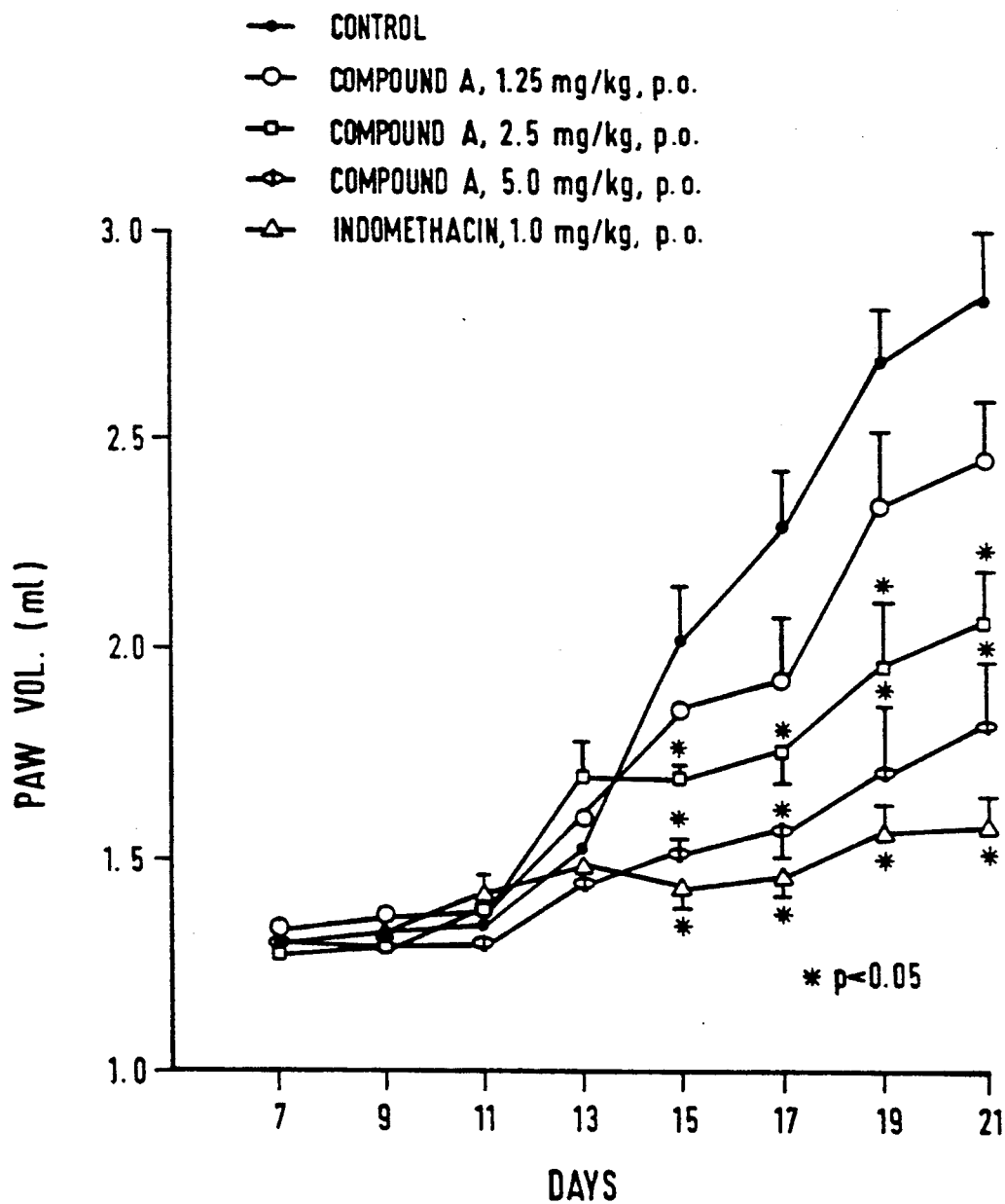
Fig. A: EFFECT OF COMPOUND A ON ADJUVANT ARTHRITIS IN RATS
NO TOXICITY OR LOSS IN WEIGHT WAS OBSERVED

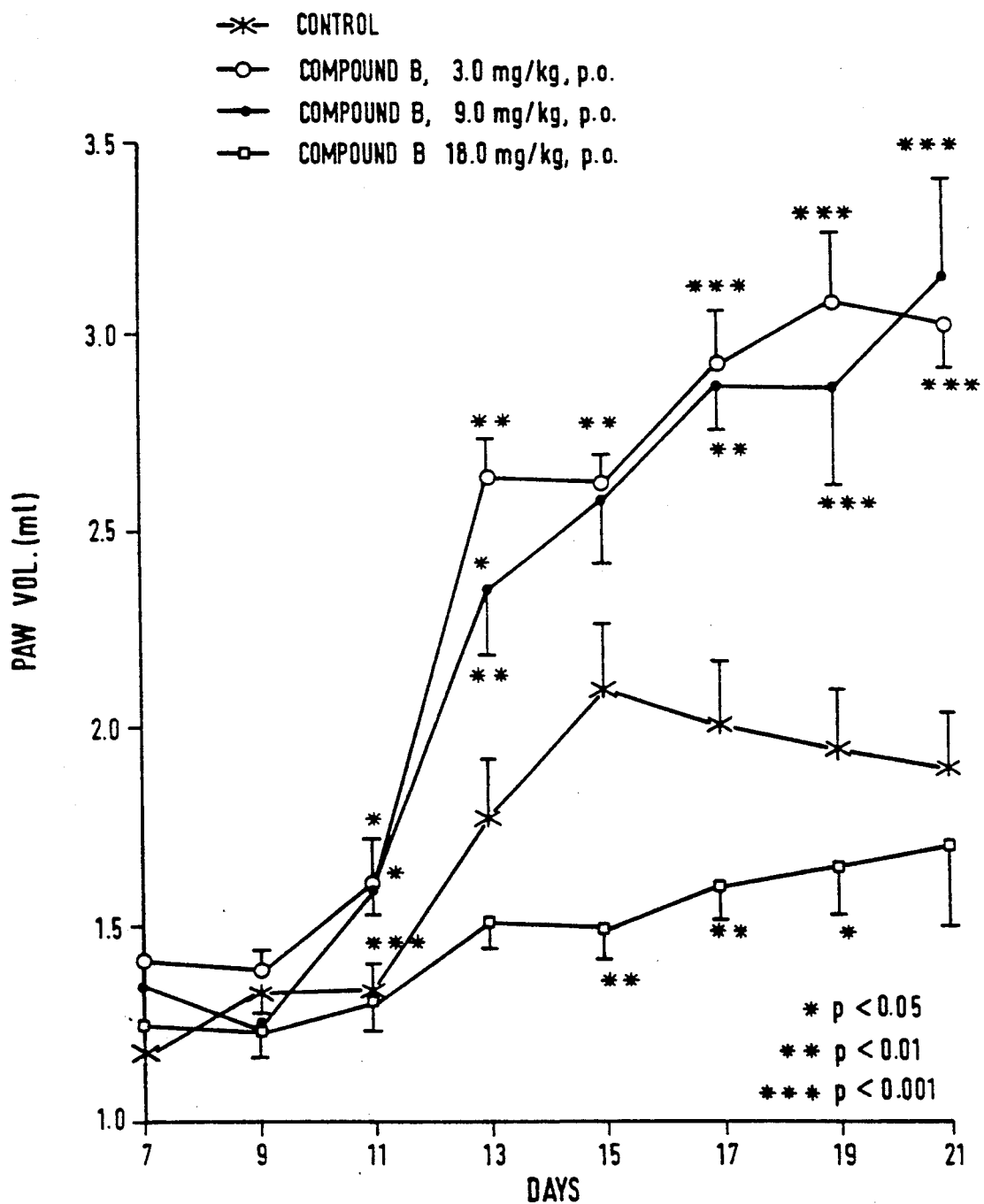

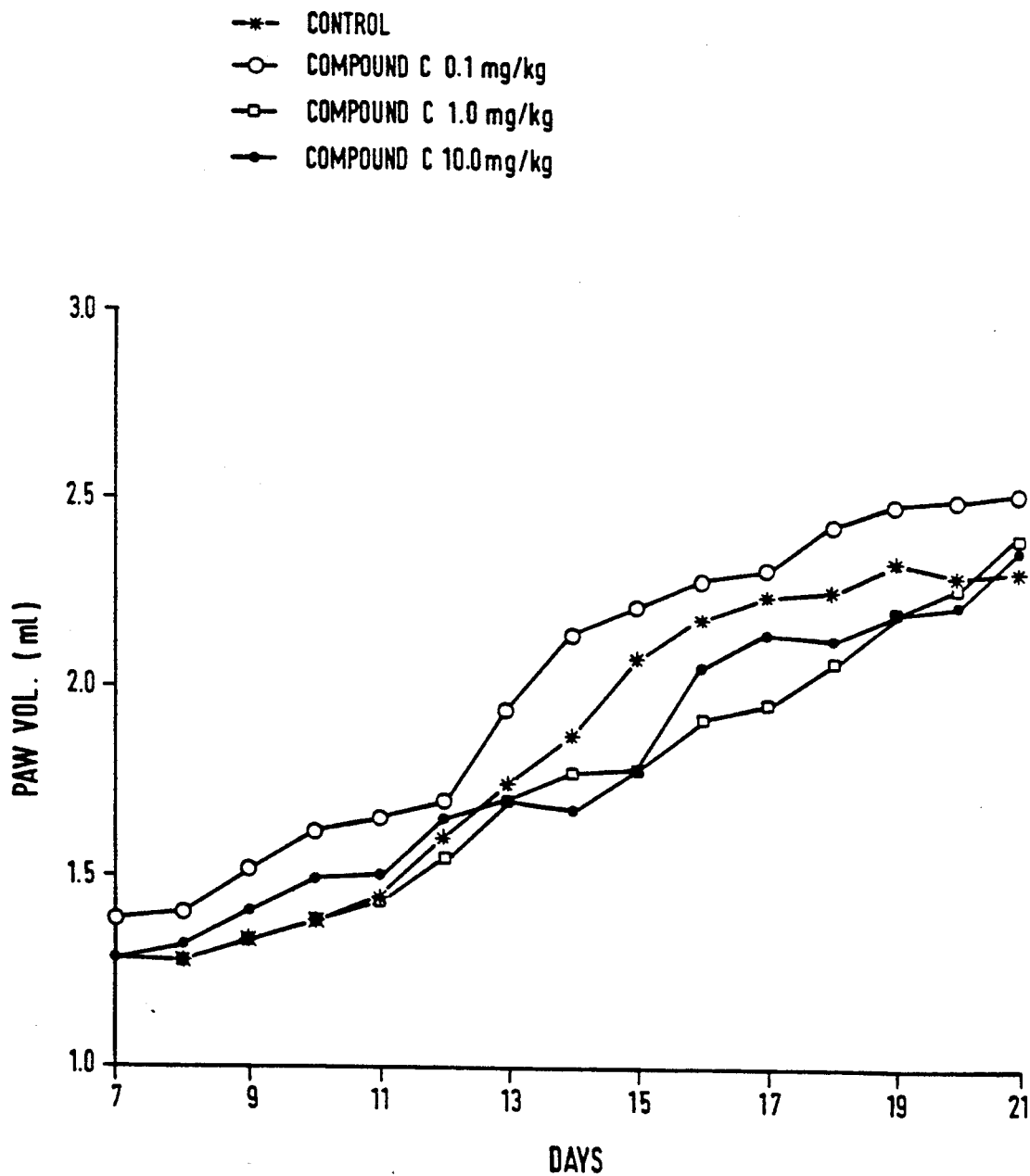

5,7-DIHYDROXY-2-METHYL-8-(4-(3-HYDROXY-1-(1-PROPYL))PIPERIDINYL)-4H-1-BENZOPYRAN-4-ONE, ITS PREPARATION AND ITS USE

DESCRIPTION

The present invention relates to 5,7-Dihydroxy-2-methyl-8-[4-(3-hydroxy-1-(1-propyl))piperidinyl]-4H-1-benzopyran-4-one (compound of formula I), its preparation and its use.

The present invention also relates to the different stereoisomers of the compound of formula I and their pharmacologically tolerable acid addition salts such as hydrochlorides, hydrobromides, sulfates, phosphates, acetates, oxalates, tartrates, citrates, maleates or fumarates.

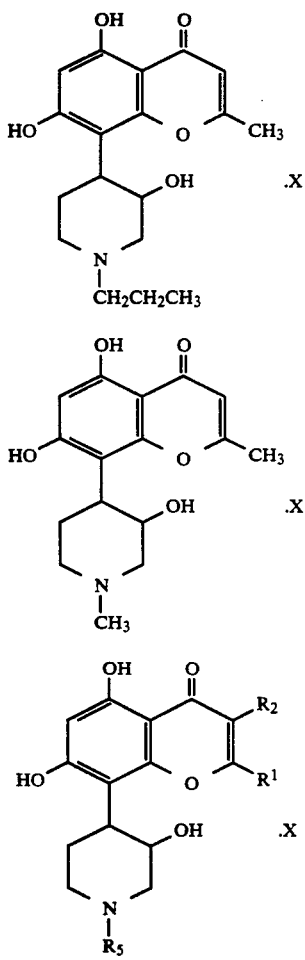

Compounds similar to the compound of formula I are already known:
1. Application EP-A-O 137 193 discloses compounds of formula II, X=various and addition salts, in the form of different stereoisomers and their use as antiflammatory agents and immunomodulators.
2. Application EP 0 241 003 discloses compounds of formula III, $R_1$=alkyl, aryl etc., $R_5$=alkyl, aralkyl etc. and X=acid addition salts and their use as antiinflammatory, analgesic and immunomodulators.
3. A publication-Harmon, A, Weiss, U. and Silverton J. V. Tetrahedron Letters 721 (1979)-discloses compounds of formula II, X=a non entity, but no biological activity.
4. A publication-Ramachandra G. Naik, et. al, Tetrahedron, 44 (7), p 2081, discloses compounds of formula II-their synthesis and their antiinflammatory activity.

A compound of formula I, while falling within the originally disclosed scope of patent application EP 0 241 003 has now been surprisingly found to display superior antiinflammatory properties in acute models of inflammation and to display novel properties in chronic models of inflammation, properties which are not characteristic of the general class of compounds described in EP 0 241 003. These properties are also not displayed by the compounds included in application No. EP-A-0 137 193.

Chronic models of inflammation such as adjuvant arthritis in rats are reflective of the human arthritic condition whereas acute models of inflammation are only indicative of the symptoms of early stages of human inflammation. A compound of formula I is superior to known compounds particularly for the treatment of chronic inflammatory conditions such as arthritis, rheumatism etc.

BRIEF DESCRIPTION OF DRAWING

FIG. A depicts the effect of cis-(+)-5,7-dihydroxy-2-methyl-8-[4-(3-hydroxy-1-(1-propyl)piperidinyl]-4H-1-benzopyran-4-one on adjuvant arthritis in rats.

FIG. B depicts the effect of compound B (formula II, EP-A-0137193), on adjuvant arthritis in rats.

FIG. C depicts the effect of compound C (formula III, EP-A-0241003), on adjuvant arthritis in rats.

DETAIL DESCRIPTION

The invention pertains to the following compounds of the formula I

TABLE 1

| S. No. | X | Sign of optical rotation | m.p. |
|---|---|---|---|
| 1 | — | cis-(+) | 210–215° C. Compound "A" |
| 2 | HCl | cis-(+) | |
| 3 | — | cis-(−) | |
| 4 | HCl | cis-(−) | |
| 5 | — | cis-(±) | |
| 6 | HCl | cis-(±) | |
| 7 | — | trans-(+) | |
| 8 | — | trans-(−) | |
| 9 | — | trans-(±) | | as well as to addition salts of said compounds. Preferred are compounds having a cis-relationship between the 3'—OH and the chromone ring. Particularly preferred compounds are:
1. cis-(+)-5,7-Dihydroxy-2-methyl-8-[4-(3-hydroxy-1-(1-propyl) piperidinyl]-4H-1-benzopyran-4-one and its hydrochloride.
2. cis-(−)-5,7-Dihydroxy-2-methyl-8-[4-(3-hydroxy-1-(1-propyl) piperidinyl]-4H-1-benzopyran-4-one and its hydrochloride.
3. cis-(+)-5,7-Dihydroxy-2-methyl-8-[4-(3-hydroxy-1-(1-propyl) piperidinyl]-4H-1-benzopyran-4-one and its hydrochloride.

A further aspect of the instant application is a process for the production of a compound of formula I, wherein a compound of formula IV

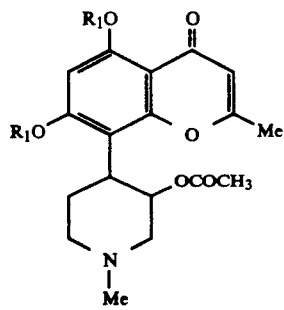

in which $R_1$ is methyl or acetyl, is (A) treated with cyanogen halogenide to give a compound of the formula V

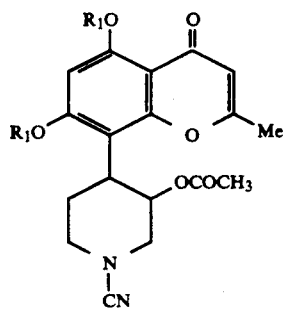

in which $R_1$ is methyl or acetyl and the compound of formula V in which $R_1$ is methyl is (B) treated with diluted mineral acid or diluted alkalihydroxide to give a compound of formula VI

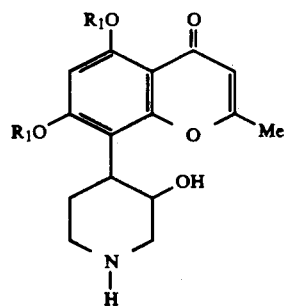

in which $R_1$ is methyl or the compound of formula V in which $R_1$ is acetyl is (C) treated with diluted mineral acid or with diluted alkali hydroxide to give a compound of formula VI in which $R_1$ is H and the compound of formula VI in which $R_1$ is methyl is (D) treated with n-propylhalogenide to give a compound of formula VII

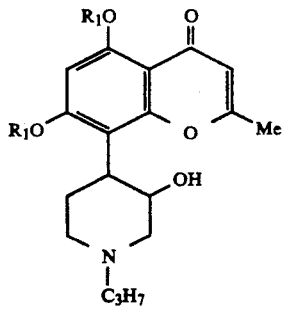

in which $R_1$ is methyl, which is transformed to a compound of formula I by heating with pyridinium-HCl, or the compound of formula VI in which $R_1$ is H is (E) treated with n-propylhalogenide to give a compound of formula I.

The preparation of a compound of formula IV is known by methods described in the application EP 0 241 003 and the publication of Ramchandra G. Naik et al., Tetrahedron 44(7), p. 2081.

Step (A) of the above process is preferably carried out with cyanogen bromide in the presence of a base such as potassium carbonate in an inert solvent such as chloroform.

Steps (B) and (C) are preferably realized with a mineral acid such as diluted hydrochloric acid or an alkali hydroxide such as diluted sodium hydroxide.

Steps (D) and (E) are preferably carried out with n-propylbromide as n-propylhalogenide in the presence of a base such as potassium carbonate in an inert solvent such as DMF.

The different stereoisomers can be obtained by the use of stereoisomeric pure starting products or by the pufification of the end product of formula I by methods known in the art or as described in EP 0 241 003.

A further aspect of the instant invention are pharmaceuticals containing an active amount of a compound of formula I as well as the use of the said compound for the treatment of rheumatism, arthritis and for the treatment of chronic inflammatory diseases.

The production of the respective pharmaceuticals and the administration thereof can occur according to methods known in the art.

The instant invention is further illustrated and characterized by the following examples and by the patent claims:

EXAMPLE 1 cis-(−)-5,7-Dimethoxy-2-methyl-8-[4'-(3'-acetoxy-1'-cyano)piperidinyl]-4H-1-benzopyran-4-one (V $R_1$=CH$_3$)

cis-(−)-5,7-Dimethoxy-2-methyl-8-[4'-(3'-hydroxy-1'-methyl)-piperidinyl]-4H-1-benzopyran-4-one (5 g) was stirred with acetic anhydride (35.0 ml) and sodium acetate (5.0 g) at 80° C. for 12 hrs. Water was added and the product was extracted with CHCl$_3$. The combined chloroform extract was dried and solvent removed under vacuum. The residue (5 g) was taken in CH$_2$Cl$_2$ (20.0 ml) and cyanogen bromide (5.60 g) was added along with potassium carbonate (7.40 g) for 2 hrs. Water was added and the product extracted with chloroform. The residue was purified by column chromatography on silica gel. 4.20 g; mp=60°–61° C.;

$[\alpha]_{Hg}^{20} = 46.82°$ (C, 0.831; Methanol).

EXAMPLE 2 cis-(−)-5,7-Dimethoxy-2-methyl-8-[4'-(3'-hydroxy)-piperidinyl]-4H-1-benzopyran-4-one (VI $R_1$=$CH_3$)

cis-(−)-5,7-Dimethoxy-2-methyl-8-[4'-(3'-acetoxy-1'-cyano) piperidinyl]-4H-1-benzopyran-4-one (1.0 g) was stirred with 2N HCl (50.0 ml) for 4 hrs. The reaction mixture was basified by addition of sod. carbonate solution and extracted with chloroform. The chloroform extract was dried and concentrated. The residue purified by crystallisation, mp.: 238°–39° C.; $[\alpha]_{Hg}^{20}$ = −130.0°, (C, 0.411; Methanol) yield: 0.630 g.

EXAMPLE 3 cis-(−)-5,7-Dimethoxy-2-methyl-8-[4'-(3'-hydroxy)-1'-(1''-propyl)) piperidinyl]-4H-1-benzopyran-4-one (VII $R_1$=$CH_3$)

cis-(−)-5,7-Dimethoxy-2-methyl-8-[4'-(3'-hydroxy)-piperidinyl]-4H-1-benzopyran-4-one (2.80 g) in dry dimethylformamide (20.0 ml) was stirred with potassium carbonate (4.0 g) and 1-propylbromide (1.18 g) at room temperature for 4 h. The reaction mixture was filtered and the residue washed with chloroform. The combined organic extract was concentrated and the residue purified by column chromatography on silica gel, 2.8 g, mp $[\alpha]_{Hg}^{20}$ = −54.95° (C, −0.740; Methanol).

EXAMPLE 4 cis-(+)-5,7-Dihydroxy-2-methyl-8-[4'-(3'-hydroxy-1'-(1''-propyl)) piperidinyl]-4H-1-benzopyran-4-one (I)

The dimethoxy compound from Example 3 (1.0 g) was heated with pyridine hydrochloride (10 g) and quinoline (1 ml) at 180° C. for 2 hrs. The reaction mixture was cooled, sat. soln of sodium carbonate was added and extracted with chloroform. The combined chloroform extract was dried, concentrated and purified by column chromatography over silica gel, to give 0.650 g of the product. mp. 237°–234°, $[\alpha]_{Hg}^{20}$ = +29.66° (C, 0.647; Methanol).

EXAMPLE 5 cis-(+)-5,7-Dihydroxy-2-methyl-8-[4'-(3'-hydroxy-1'-(1''-propyl)) piperidinyl]-4H-1-benzopyran-4-one (I)

cis-(+)-5,7-Dihydroxy-2-methyl-8-[4'-(3'-hydroxy)-piperidinyl]-4H-1-benzopyran-4-one (0.26 g) in dry dimethylformamide (20.0 ml) was stirred with potassium carbonate (4.0 g) and 1-propyl bromide (1.18 g) at room temperature for 4 h. The reaction mixture was filtered and the residue washed with chloroform. The combined organic extract was concentrated and the residue purified by column chromatography on silica gel, to give 0.24 g of the compound, mp 237°–238° C. $[\alpha]_{Hg}^{20}$ = =30.1° (C=0.61, MeOH).

The superiority of a compound of the invention over a representative compound of the prior art is described in the following paragraphs. For convenience the preferred compound No. 1 of Table 1 is called compound 'A' and is chosen as a representative compound to serve as an example in such studies. The compound of the prior art EP-A-0 137 193, formula II, X=HCl will be referred to as compound 'B' and one of the most potent compound and a representative compound mentioned in the application EP 0 241 003, formula III, $R_1$=Ph, $R_2$=H, $R_5$=$CH_3$, X=HCl, will be referred to as compound 'C'.

1. Acute inflammation model:

Systemic anti-inflammatory action on carrageenin-induced paw oedema in rats.

Male Charles Foster rats (120–150 g) were fasted for 18 hours, with water ad libitum. The test compound suspended in Tween$^R$ 80 and 0.5% C.M.C. was administered orally. The control group received Tween 80 and 0.5% C.M.C. 0.05 ml of 0.5% carrageenin suspension was injected subcutaneously into the plantar region of the left hind paw. Using a Maclab differential volume meter, the paw volume was determined before the carrageenin injection and 3 and 6 hours after the injection. The percentage decrease in paw volume was calculated by the following equation:

$$\frac{\text{Vehicle control mean edema volume} - \text{Test Group mean edema volume}}{\text{Vehicle control mean edema volume}} \times 100 =$$

% decrease in paw volume

The $ED_{50}$ value was calculated from the dose/response curve. Six animals were used for each group. The results are summarized in Table 2.

TABLE 2

| Comp. | $ED_{50}$, mg/kg p.o. | Rat, $LD_{50}$ mg/kg, p.o. | Therapeutic index ($LD_{50}ED_{50}$) |
|---|---|---|---|
| A | 20.0 | 650.0 | 32.5 |
| B | 9.0 | 82.5 | 9.4 |
| C | 1.3 | 27.0 | 20.76 |

Compound A clearly showed a favourable therapeutic index over compounds B and C.

2. Adjuvant induced arthritis (developing) in Rats
Method

Female Charles Foster rats weighing 150–180 g were sorted into groups (10 rats/group). Each animal received 10 μl of 1% suspension of mycobacterium tuberculli in paraffin oil, intradermally, at the base of the tail. Drug treatment was instituted on the day of the induction of arthritis and continued for 21 days. The body weight of each rat was noted prior to the adjuvant suspension injection and subsequently all throughout for 21 days. Volumes of both hind paws were recorded on the day of injection and subsequently from 7 days onwards till the end of the experiment.

Results:

Compound B was administered at the daily dose of 3, 9, 18 and 27 mg/kg, p.o. for 21 days. A biphasic response was observed. At the dose of 3 and 9 mg/kg, p.o. per day 58.6% and 64.9% potentiation of the secondary arthritic response was observed. The 18 mg/kg. p.o./-day dose produced significant inhibition, however, in this group of rats symptoms of cytotoxicity such as weight loss and severe diarrhoea were observed. In the 27 mg/kg, p.o./day all the rats died by the end of the 8th day indicating a narrow therapeutic range for this compound, FIG. B. The inhibition that is observed in the 18 mg/kg, p.o. group may be due to toxicity.

Compound C was tested at doses 0.1, 1 and 10 mg/kg, p.o. over a period of 21 days. No inhibition of adjuvant arthritis was seen at any of the doses tested. 50% mortality was seen when the compound was administered at 10 mg/kg, p.o./day between 9th and 11th day of administration, FIG. C.

Compound A of the present invention was tested at the daily doses of 1.25, 2.5, 5 and 10 mg/kg, p.o. over a period of 21 days. A dose-dependent and significant inhibition of adjuvant arthritis was observed, FIG. A.

Compound A was administered at 30 mg/kg, p.o./day over a period of 21 days. No deaths or toxic side effects were observed.

We claim:

1. 5,7-Dihydroxy-2-methyl-8-[4-(3hydroxy-1-(1-propyl)piperidinyl]-4H-1-benzopyran-4-one, a compound of formula I

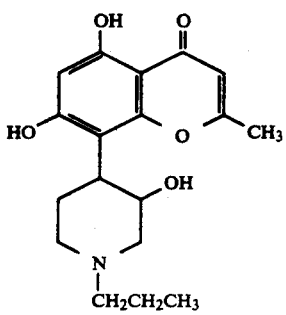

the stereoisomers and the pharmacologically tolerable acid addition salts thereof.

2. Cis-(+)-5,7-Dihydroxy-2-methyl-8-[4-(3-hydroxy-1-(1-propyl)piperidinyl]-4H-1-benzopyran-4-one and its hydrochloride,
   cis-(−)-5,7-Dihydroxy-2-methyl-8-[4-(3-hydroxy-1-(1-propyl)piperidinyl]-4H-1-benzopyran-4-one and its hydrochloride and
   cis-(±)-5,7-Dihydroxy-2-methyl-8-[4-(3-hydroxy-1-(1-propyl)piperidinyl]-4H-1-benzopyran-4-one and its hydrochloride.

3. A pharmaceutical containing an active amount of a compound as claimed in claim 1.

4. A method of treating rheumatism which comprises administering to a host in need thereof an amount of the compound according to claim 1 effective to treat rheumatism.

5. A method of treating arthritis which comprises administering to a host in need thereof an amount of the compound according to claim 1, effective to treat arthritis.

6. A method of treating chronic inflammatory diseases which comprises administering to a host in need thereof an amount of the compound according to claim 1 effective to treat chronic inflammatory diseases.

* * * * *

UNITED STATES PATENT AND TRADEMARK OFFICE
CERTIFICATE OF CORRECTION

PATENT NO. : 5,292,751
DATED : March 08, 1994
INVENTOR(S) : Ramachandra G. NAIK et al It is certified that error appears in the above-indentified patent and that said Letters Patent is hereby corrected as shown below:

On title page, item [54] and col. 1, lines 1 and 2 change "(" (first occurrence) and ")" (last occurrence) to --[-- and --]-- respectively.

Claim 1, Column 7, Line 1, between "3" and "hydroxy" insert a hyphen (-).

Claim 5, Column 8, Line 20, delete the comma (,).

Signed and Sealed this

Sixth Day of December, 1994

BRUCE LEHMAN

Attest:

Attesting Officer

Commissioner of Patents and Trademarks